(12) United States Patent
Zou et al.

(10) Patent No.: US 12,343,434 B2
(45) Date of Patent: Jul. 1, 2025

(54) HYBRID MEMBRANE CAMOUFLAGED NANOMEDICINE LOADED WITH OXIDATIVE PHOSPHORYLATION INHIBITOR AND PREPARING METHOD THEREOF

(71) Applicant: Henan University, Henan (CN)

(72) Inventors: Yan Zou, Henan (CN); Yajing Sun, Henan (CN); Bingyang Shi, Henan (CN); Meng Zheng, Henan (CN); Mingcong Hao, Henan (CN)

(73) Assignee: Henan University, Henan (CN)

( * ) Notice: Subject to any disclaimer, the term of this patent is extended or adjusted under 35 U.S.C. 154(b) by 229 days.

(21) Appl. No.: 17/739,090

(22) Filed: May 7, 2022

(65) Prior Publication Data
US 2022/0378712 A1 Dec. 1, 2022

(30) Foreign Application Priority Data
May 19, 2021 (CN) .......................... 202110555902.1

(51) Int. Cl.
*A61K 9/51* (2006.01)
*A61K 9/50* (2006.01)
(Continued)

(52) U.S. Cl.
CPC .......... *A61K 9/5176* (2013.01); *A61K 9/5068* (2013.01); *A61K 9/5073* (2013.01);
(Continued)

(58) Field of Classification Search
CPC ................ A61K 9/5176; A61K 9/5146; A61K 31/4184; A61K 9/5068; A61K 9/5073;
(Continued)

(56) References Cited

U.S. PATENT DOCUMENTS

2013/0337066 A1* 12/2013 Zhang ..................... A61P 35/00
424/234.1
2019/0298659 A1* 10/2019 Gu ............................ A61P 3/10

FOREIGN PATENT DOCUMENTS

CN 110478332 A * 11/2019

OTHER PUBLICATIONS

Florea et al. Cancers 3.1 (2011): 1351-1371. (Year: 2011).*
(Continued)

*Primary Examiner* — Sue X Liu
*Assistant Examiner* — Sarah C Wistner

(57) ABSTRACT

The disclosure provides a hybrid membrane camouflaged nanomedicine loaded with oxidative phosphorylation inhibitor and preparation method thereof. The nanomedicine comprises an inner core and an outer shell coated on the periphery of the inner core. The inner core is a ROS-responsive drug-loaded nanoparticle, and the drug loaded by the ROS-responsive nanocarrier is an oxidative phosphorylation inhibitor. The outer shell is a hybrid membrane of mitochondrial membrane and cancer cell membrane. The nanomedicines can cross the BBB and reach tumor sites by the homologous targeting of cancer cell membrane, and then they can homologously target and enter mitochondria by the mitochondrial membrane. Subsequently, under the high-level ROS environment of the mitochondria, the ROS responsive drug-loaded nanoparticle releases the oxidative phosphorylation inhibitor due to the swell and degradation of the inner core, so that the safe and efficient targeted GBM therapy is achieved.

20 Claims, 17 Drawing Sheets
(2 of 17 Drawing Sheet(s) Filed in Color)

(51) Int. Cl.
*A61K 31/4184* (2006.01)
*A61P 35/00* (2006.01)

(52) U.S. Cl.
CPC ........ *A61K 9/5146* (2013.01); *A61K 31/4184* (2013.01); *A61P 35/00* (2018.01)

(58) Field of Classification Search
CPC ........... A61K 47/34; A61P 35/00; B82Y 5/00; B82Y 30/00; B82Y 40/00
See application file for complete search history.

(56) References Cited

OTHER PUBLICATIONS

Rao et al. ACS nano 11.4 (2017): 3496-3505. (Year: 2017).*
Jiang et al. Biomaterials 192 (2019) 292-308. (Year: 2019).*
Barouti et al. Progress in Polymer Science 73 (2017) 1-31. (Year: 2017).*
Zheng, M., 'ROS-Responsive Polymeric siRNA Nanomedicine Stabilized by Triple Interactions for the Robust Glioblastoma Combinational RNAi Therapy,' Jul. 26, 2019, pp. 1-9. Wiley-VCH [online]. (Year: 2019).*

Nanomaterial Biointerfacing via Mitochondrial Membrane Coating for Targeted Detoxification and Molecular Detection Hua Gong, Qiangzhe Zhang, Anvita Komarla, Shuyan Wang, Yaou Duan, Zhidong Zhou, Fang Chen, Ronnie H. Fang, Sheng Xu, Weiwei Gao, and Liangfang Zhang Nano Lett. 2021, 21, 6, 2603-2609.
Regulating intracellular fate of siRNA by endoplasmic reticulum membrane-decorated hybrid nanoplexes Chong Qiu 1, Hu-Hu Han 1, Jing Sun1, Hai-Tao Zhang2, Wei Wei1, Shi-He Cui1, Xin Chen 1, Jian-Cheng Wang 1 & Qiang Zhang1 Nature Communications vol. 10, Article No. 2702 (2019).
Gboxin is an oxidative phosphorylation inhibitor that targets glioblastoma Yufeng Shi1,2, S. Kyun Lim3,4,8, Qiren Liang3, Swathi V. Iyer1,2, Hua-Yu Wang3, Zilai Wang1,2, Xuanhua Xie1,2, Daochun Sun1,2, Yu-Jung Chen1,2,5, Viviane Tabar1,6, Philip Gutin1,6, Noelle Williams3, Jef K. De Brabander3 & Luis F. Parada1,2,6,7* Nature vol. 567, pp. 341-346 (2019).
Erythrocyte-Platelet Hybrid Membrane Coating for Enhanced Nanoparticle Functionalization Diana Dehaini, Xiaoli Wei, Ronnie H. Fang, Sarah Masson, Pavimol Angsantikul, Brian T. Luk, Yue Zhang, Man Ying, Yao Jiang, Ashley V. Kroll, Weiwei Gao, and Liangfang Zhang* Adv. Mater. 2017, 1606209.

* cited by examiner

HYBRID MEMBRANE CAMOUFLAGED NANOMEDICINE LOADED WITH OXIDATIVE PHOSPHORYLATION INHIBITOR AND PREPARING METHOD THEREOF

TECHNICAL FIELD

The disclosure relates to the technical field of drug carriers, in particular to a hybrid membrane camouflaged nanomedicine loaded with an oxidative phosphorylation inhibitor and preparing method thereof.

BACKGROUND ART

Mitochondria, two-layered membrane-coated organelles present in most cells, are suppliers of power and energy for mammals. In addition to powering cells, they are also involved in processes such as cell differentiation, cell information transmission, and apoptosis. In recent years, targeting mitochondria has been considered as a promising strategy for tumor therapy.

Currently, Gboxin is a mitochondrial oxidative phosphorylation inhibitor specific to glioblastoma (GBM), and the mechanism of action is as follows: Gboxin binds to ATP synthase on the inner mitochondrial membrane, thereby inactivating ATP synthase and reducing ATP synthesis; and further the electron transfer in an oxidative phosphorylation process is blocked, thereby changing the membrane potential of mitochondria, damaging the structure of mitochondria, promoting accelerated release of cytochrome C (CytC) in the mitochondrial membrane gap into cytoplasm so as to further activate apoptosis protein families (Caspase 3 and 9) in the cytoplasm, thereby finally fulfilling low-concentration and high-efficiency killing of GBM cells. However, Gboxin suffers from the drawback of extremely short blood half-life, which also severely hampers its application in the GBM therapy.

With the rapid development of biomedicine, nanotechnology-based drug delivery systems provide new ideas. Compared with free anticancer drugs, nanoparticles have multiple advantages such as protecting drugs from enzymatic degradation in vivo, promoting drugs to pass through various biological barriers, improving the drug solubility, and prolonging in vivo circulation time. Meanwhile, traditional nanomedicines, as foreign substances of the organism, are easily recognized and eliminated by immune systems in vivo, and have certain potential toxic and side effects on the liver and kidney, which significantly restricts the development of nano-delivery systems.

Given this, the disclosure is particularly proposed.

DISCLOSURE

The disclosure aims to provide a hybrid membrane camouflaged nanomedicine loaded with an oxidative phosphorylation inhibitor and preparing method thereof so as to solve the above technical problems.

Inspired by the natural ecosystem, the concept of biomembrane bionics has been gradually applied to practical research from the ideal hypothesis, that is, various biomembranes are extracted to be coated on the surface of the nanomedicine to form a biomimetic nanosystem. The erythrocyte membrane can avoid phagocytosis of immunocytes, and prolong circulation time in vivo. Specific proteins and receptors (Thomsen, Friedenreich (TF) antigen), epithelial cell cadherin (E-cadherin) and membrane proteins including CD47 exist on the surface of cancer cell membrane, which prevents nanomedicines from elimination by the immune system while fulfilling homologous targeting. Immune cell membrane can achieve immune escape and target inflammatory sites, and at the same time, they can also effectively activate the tumor immunosuppressive microenvironment to eliminate cancer cells through the immune system. The organelle membranes can also achieve immune escape and improve biocompatibility while having the capability of homologous targeting.

The inventors propose the mitochondrial-cancer cell hybrid membrane camouflaged nanomedicine loaded with a tumor inhibition drug in order to anticipate the feasibility of treating cancer.

The disclosure is achieved by the following steps.

The disclosure provides a mitochondrial-cancer cell hybrid membrane camouflaged nanomedicine loaded with oxidative phosphorylation inhibitor, which comprises an inner core and an outer shell, in which the outer shell is coated on a periphery of the inner core, the inner core is a ROS-responsive drug-loading nanoparticle, a drug loaded by the ROS-responsive drug-loading nanoparticle is an oxidative phosphorylation inhibitor, and the outer shell is a hybrid membrane of a mitochondrial membrane and a cancer cell membrane. ROS is reactive oxygen species.

In a preferred embodiment of the disclosure, the oxidative phosphorylation inhibitor is Gboxin, namely, 1-carboxymethyl-2-ethyl-3-methyl-1H-benzimidazole-3-ammonium L-menthol ester chloride, and has a following structural formula:

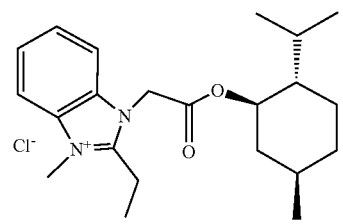

In a preferred embodiment of the disclosure, the ROS-responsive drug-loading nanoparticle is based on a ROS-responsive high-molecular polymeric nanocarrier.

Preferably, the ROS-responsive high-molecular polymeric nanocarrier is a diblock polymer.

Preferably, the diblock polymer is polyethylene glycol-poly(β-butyrolactone), having a following structural formula:

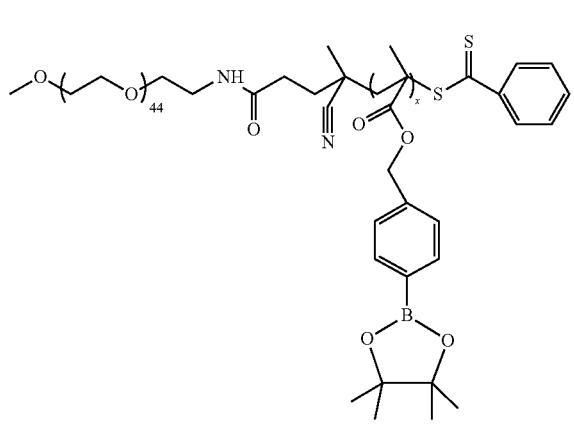

Preferably, a polymerization degree of poly(β-butyrolactone) in the polyethylene glycol-poly(β-butyrolactone) is 8-12, the poly(β-butyrolactone) has a molecular weight of $2.4 \times 10^3$-$3.6 \times 10^3$, and a total molecular weight is $4.4 \times 10^3$-$5.6 \times 10^3$. The polyethylene glycol-poly(β-butyrolactone) is PEG-PHB.

In a preferred embodiment of the disclosure, a drug loading capacity of the oxidative phosphorylation inhibitor in the inner core is 4.4%-36%.

Preferably, a drug loading capacity of Gboxin in the inner core is 4.4%-36%.

In a preferred embodiment of the disclosure, the cancer cell membrane is derived from a GBM cell or a glioma stem cell.

Preferably, a protein weight ratio of the mitochondrial membrane to the cancer cell membrane is 1:1.

In a preferred embodiment of the disclosure, a mass ratio of the inner core to the outer shell is 1:1; an average particle size of the inner core is 50-70 nm, and an average particle size of the mitochondrial-cancer cell hybrid membrane camouflaged nanomedicine loaded with oxidative phosphorylation inhibitor is 80-100 nm.

The disclosure provides a preparing method of the mitochondria-cancer cell hybrid membrane camouflaged nanomedicine loaded with oxidative phosphorylation inhibitor, which comprises: mixing the mitochondrial-cancer cell hybrid membrane with the inner core so that the hybrid membrane is coated on the periphery of the inner core.

In a preferred embodiment of the disclosure, the preparing method comprises preparing the inner core, and preparing the inner core comprises mixing of the oxidative phosphorylation inhibitor and the ROS-responsive high-molecular polymeric nanocarrier, stirring and/or dialysis.

Preferably, the ROS-responsive high-molecular polymeric nanocarrier is dissolved in a water miscible solvent such as THF or DMSO, being added with the oxidative phosphorylation inhibitor, followed by stirring until a reaction is completed and dialysis to remove a free oxidative phosphorylation inhibitor.

In a preferred embodiment of the disclosure, the preparing method comprises preparing the outer shell, and preparing the outer shell comprises mixing, ultrasonic treatment and/or extrusion of the mitochondria membrane and the cancer cell membrane.

Preferably, the ultrasound treatment is carried out for 8-10 minutes (min) at an ultrasound frequency of 100-110 W and a temperature of 36-38° C.

In a preferred embodiment of the disclosure, the extrusion is performed through a series of water-phase filters, and preferably, the extrusion is repeatedly performed 7 times through the water-phase filters with reducing pore sizes of 800 nm, 400 nm and 200 nm in turn.

The disclosure provides a use of the mitochondria-cancer cell hybrid membrane camouflaged nanomedicine loaded with oxidative phosphorylation inhibitor or the nanomedicine prepared by the above-mentioned preparation method in treating a tumor or activating a mitochondria apoptosis.

Preferably, the tumor is GBM.

Preferably, the oxidative phosphorylation inhibitor for activating mitochondria apoptosis is an inhibitor that can promote changes in mitochondrial membrane potential and/or an inhibitor that can inhibit ATP synthase activity.

The disclosure also provides an inner core for the mitochondria-cancer cell hybrid membrane camouflaged nanomedicine loaded with oxidative phosphorylation inhibitor, the inner core is a ROS responsive drug-loading nanoparticle, and a drug loaded by the ROS responsive nanoparticle is an oxidative phosphorylation inhibitor; and preferably, the oxidative phosphorylation inhibitor is Gboxin.

The disclosure has the following advantageous effects.

The mitochondrial-cancer cell hybrid membrane camouflaged nanomedicine loaded with oxidative phosphorylation inhibitor is a biomimetic targeting nanomedicine, which can cross BBB and reach the tumor sites with the homologous targeting property of the cancer cell membrane, and then the nanomedicine can homologously target and enter mitochondria with the mitochondrial membrane. Subsequently, under high_level ROS in the mitochondria, the ROS responsive drug-loading nanoparticle s swell and degrade to release the loaded drug, i.e., oxidative phosphorylation inhibitor, thereby achieving safe and robust targeted cancer therapy. The nanomedicine is coated by the outer shell so that the defect of the short half-life period of the loaded drug in the blood is avoided, and the long blood circulation of the drug is favorably protected.

Specific proteins and receptors (Thomsen, Friedenreich (TF) antigen), epithelial cell cadherins (E-cadherin) and membrane proteins including CD47 exist on the surface of the cancer cell membrane, which prevents the nanomedicines from elimination by the immune system while fulfilling homologous targeting. In other words, the cancer cell membrane can fulfill immune escape and target inflammatory sites, and at the same time, it can also effectively activate the tumor immunosuppressive microenvironment to eliminate cancer cells through the immune system.

The prepared mitochondrial apoptosis activator based on the above-mentioned nanomedicine can kill tumor cells by activating mitochondrial apoptosis pathways, so that the safe and robust chemotherapy of tumors is achieved.

BRIEF DESCRIPTION OF DRAWINGS

In order to more clearly illustrate the technical solutions of the embodiments of the disclosure, the drawings used in the embodiments will be briefly described below. It should be understood that the following drawings only illustrate some embodiments of the disclosure, and thus, they should not be considered as a limit of the scope, and for those skilled in the art, other related drawings can be obtained according to the drawings without inventive efforts. The application file contains at least one drawing executed in color. Copies of this patent application publication with color drawing(s) will be provided by the Office upon request and payment of the necessary fee.

BEST MODE

Reference of embodiments of the disclosure will now be provided in detail, of which one or more examples are described below. Each example of the disclosure is provided by way of explanation, not limitation. In fact, it will be apparent to those skilled in the art that various modifications and variations can be made in the disclosure without departing from the scope or spirit of the disclosure. For instance, features illustrated or described as part of one embodiment, can be used on another embodiment to yield a still further embodiment.

The disclosure provides a mitochondria-cancer hybrid membrane camouflaged nanomedicine loaded with an oxidative phosphorylation inhibitor, which comprises an inner core and an outer shell, in which the outer shell is coated on the periphery of the inner core. The inner core is a ROS-responsive drug-loading nanoparticle, and the drug loaded by the ROS-responsive nanoparticle is the oxidative phosphorylation inhibitor. The outer shell is a hybrid membrane of a mitochondrial membrane and a cancer cell membrane.

The coating of the outer shell to the inner core is achieved by the physical extrusion and/or ultrasonic of the inner core and the outer shell. The outer shell is coated on the periphery of the inner core, and the homologous targeting to mitochondria and tumor cells is respectively fulfilled through the mitochondria membrane and the cancer cell membrane.

The ROS level in tumor cells is obviously higher than that of normal cells and tissues, and mitochondria have the highest ROS level in the tumor cells, and thus, in the disclosure, the ROS-responsive nanoparticles loaded with the oxidative phosphorylation inhibitor are specially provided to prepare the inner core, so that the loaded drug can be released with the stimulation of the high ROS level.

The cancer cell membrane can be derived from various tumors such as lung cancer, brain glioma, lymphoma, gastric cancer, esophageal cancer, nasopharyngeal cancer, colorectal cancer, hepatocarcinoma, breast cancer, cervical cancer, leukemia and so on.

In a preferred embodiment of the disclosure, the oxidative phosphorylation inhibitor is Gboxin, which is 1-carboxymethyl-2-ethyl-3-methyl-1H-benzimidazol-3-ammonium L-menthol ester chloride having the following structural formula:

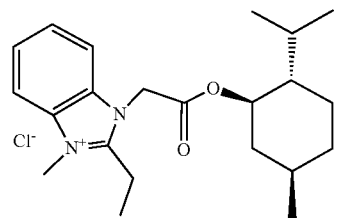

In other embodiments, the inner core can be loaded with any drugs that inhibit mitochondrial function to activate apoptosis in tumor cells.

Figure 1:
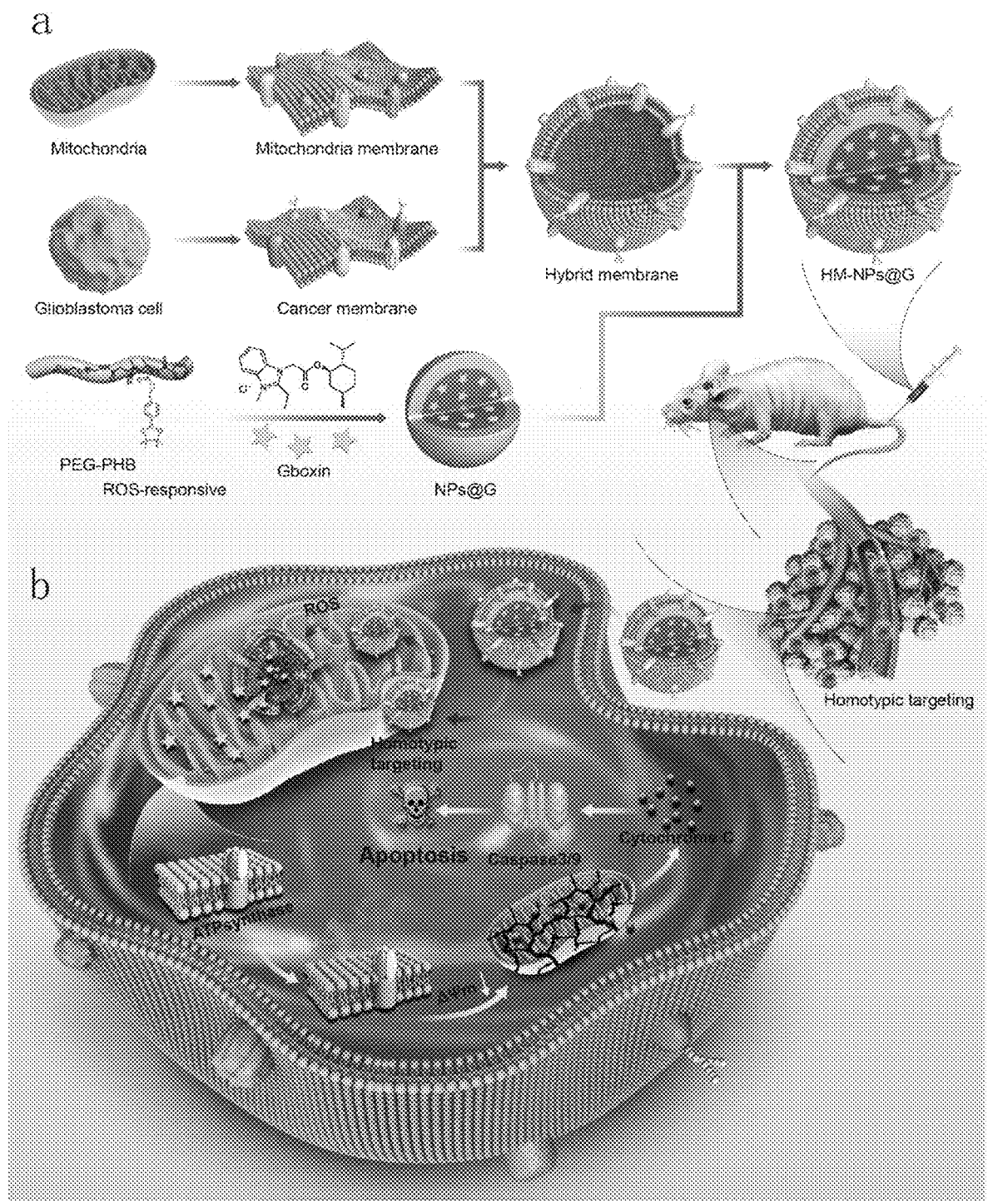
FIG. 1 shows the schematic view of preparation, accumulation at tumor sites, intracellular release and exertion of drug effect of the nanomedicine when the oxidative phosphorylation inhibitor is Gboxin.

FIG. 1 is a schematic view showing the preparation, accumulation in tumor sites, intracellular release and exertion of drug effect of the nanomedicine when the oxidative phosphorylation inhibitor is Gboxin. As shown in (a), the cancer cell membrane and the mitochondrial membrane are extracted, and the hybrid membrane (HM) is prepared by means of ultrasound treatment and physical extrusion. Meanwhile, the ROS-responsive nanoparticles (PEG-PHB) encapsulate Gboxin by the self-assembly method, and then is mixed with HM by the extrusion method to obtain HM-NPs@G; in (b), the nanomedicines cross BBB and reach the tumor site by utilizing the homologous targeting property of the cancer cell membrane through a long circulation. After being uptaken by tumor cells in a targeted manner, the nanomedicines further target and enter mitochondria by utilizing the homologous targeting of the mitochondria membrane. In the mitochondria, the nanoparticles of the PEG-PHB swell and degrade in the high-level ROS environment to release Gboxin. The released and accumulated Gboxin kills tumor cells by activating the mitochondria-related apoptosis pathway, achieving the safe and efficient chemotherapy of GBM.

Gboxin can combine with the ATP synthase in the mitochondria and inactivating it, further reducing ATP synthesis and blocking electron transfer in the oxidative phosphorylation process, so that mitochondria membrane potential is changed, which causes mitochondrial structure disruption. Then, cytochrome C (CytC) in the mitochondria membrane gap is accelerated to release into cytoplasm, and the CytC further activates apoptosis protein families (Caspase 3 and Caspase 9) in the cytoplasm, and finally glioma cells are killed. The intelligent biomimetic nanomedicines can safely and efficiently kill glioma cells through the above reaction mechanism, and are expected to successfully cure GBM.

In a preferred embodiment of the disclosure, the ROS-responsive drug-loading nanoparticle is based on a ROS-responsive high-molecular polymeric nanocarrier.

Preferably, the ROS-responsive high-molecular polymeric nanocarrier is a diblock polymer.

It should be noted that, in other embodiments, the ROS-responsive drug-loading nanoparticle is not limited to a diblock polymer, for example, it may be a triblock polymer, as long as it is a polymer having a ROS-responsive block.

Preferably, the diblock polymer is polyethylene glycol-poly(β-butyrolactone).

Preferably, the polymerization degree of poly(β-butyrolactone) in the polyethylene glycol-poly(β-butyrolactone) is 8-12, poly(β-butyrolactone) has a molecular weight of $2.4 \times 10^3$-$3.6 \times 10^3$, and polyethylene glycol-poly(β-butyrolactone) has a total molecular weight of $4.4 \times 10^3$-$5.6 \times 10^3$. The polyethylene glycol-poly(β-butyrolactone) is PEG-PHB.

Preferably, the polymerization degree of poly(β-butyrolactone) in the polyethylene glycol-poly(β-butyrolactone) is 11, poly(β-butyrolactone) has a molecular weight of 3.3×10³, and polyethylene glycol-poly(β-butyrolactone) has a total molecular weight of 5.3×10³.

In a preferred embodiment of the disclosure, the drug loading capacity of the oxidative phosphorylation inhibitor in the inner core is 4.4%-36%. For example, it can be 10%, 11%, 12%, 15%, 18%, 20%, 25%, 30%.

Preferably, the drug loading capacity of Gboxin in the inner core is 4.4%-36%. For example, it can be 10%, 11%, 12%, 15%, 18%, 20%, 25%, 30%, 36%. The inventor finds that when the theoretical drug loading capability is 10%, 20% and 30%, respectively, the drug loading efficiency is 41.5%, 70.4% and 44.9%, respectively.

In a preferred embodiment of the disclosure, the cancer cell membrane is derived from GBM cells or GBM stem cells.

Preferably, the protein weight ratio of the mitochondrial membrane to the cancer cell membrane is 1:1; and when the mixing mass ratio is 1:1, the effect of the hybrid membrane is optimal.

In a preferred embodiment of the disclosure, the mass ratio of the inner core to the outer shell is 1:1; the average particle size of the inner core is 50-70 nm, and the average particle size of the final nanomedicines is 80-100 nm.

The disclosure provides a preparing method of a mitochondria-cancer cell hybrid membrane camouflaged nanomedicine loaded with the oxidative phosphorylation inhibitor loaded, which comprises: mixing the hybrid membrane of the mitochondrial membrane and the cancer cell membrane with the inner core so that the hybrid membrane is coated on the periphery of the inner core. The coating of the inner core with the hybrid membrane can be achieved by ultrasonic and/or extrusion. The ultrasonic treatment is carried out for 8-10 min at the ultrasonic frequency of 100-110 W and the temperature is 36-38° C.

In one embodiment, the hybrid membrane of the mitochondrial membrane and the cancer cell membrane is mixed with the inner core, then ultrasonic treatment (for example, ultrasonic treatment for 1-10 min) is firstly performed, and then the extrusion is repeatedly performed 7 times through the water-phase filters with reducing pore sizes of 800 nm, 400 nm and 200 nm in turn.

In a preferred embodiment of the disclosure, the preparing method further comprises preparing the inner core, wherein preparing the inner core comprises mixing the oxidative phosphorylation inhibitor with the ROS-responsive high-molecular polymeric nanocarrier; and preferably, the ROS-responsive high-molecular polymeric nanocarriers are dissolved in a water miscible solvent, being added with the oxidative phosphorylation inhibitor, followed by stirring until a reaction is completed and dialysis to remove the free oxidative phosphorylation inhibitor. The water miscible solvents are various solvents such as tetrahydrofuran (THF) or DMSO, and the particle size when using tetrahydrofuran is more preferable.

In one embodiment, the outer shell is prepared by the following method: mixing the mitochondrial membrane with the cancer cell membrane, performing ultrasonic treatment in ice bath for 2 min, repeatedly extruding under 800 nm, 400 nm and 200 nm of water-phase filters, and centrifuging (4° C., 21,000×g, 30 min) to obtain the mitochondrial-cancer cell hybrid membrane. In addition, the mixing process is only one of the preparation process parameters listed by the inventor, and in practical application, the preparation time and the type of the selected water-phase filter can be adaptively adjusted according to needs.

The disclosure provides a use of the mitochondrial-cancer cell hybrid membrane camouflaged nanomedicine loaded with an oxidative phosphorylation inhibitor or the nanomedicine prepared by the above preparing method in treating tumor or activating mitochondria apoptosis; preferably, the tumor is GBM.

The preparation and use of the above-mentioned tumor treatment drugs include but not limited to the effects such as tumor focus elimination, tumor scope reduction, anti-tumor, tumor drug resistance treatment.

The disclosure provides a mitochondrial apoptosis-related inhibitor, which comprises a mitochondria-cancer cell hybrid membrane camouflaged nanomedicine loaded with an oxidative phosphorylation inhibitor or a nanomedicine prepared by the above preparation method.

Preferably, the mitochondrial apoptosis-related inhibitor can promote changes in mitochondrial membrane potential and/or inhibit ATP synthase activity.

The disclosure also provides an inner core for nanomedicines, the inner core is a ROS-responsive drug-loading nanoparticle, and the drug loaded by the nanoparticles is an oxidative phosphorylation inhibitor; and preferably, the oxidative phosphorylation inhibitor is Gboxin.

In order to make the objects, technical solutions and advantages of the embodiments of the disclosure clearer, the technical solutions in the embodiments of the disclosure will be clearly and completely described below. The examples, in which specific conditions are not specified, were conducted under conventional conditions or conditions recommended by the manufacturer. The reagents or instruments used are not indicated by the manufacturer, and are all conventional products available commercially.

The features and properties of the disclosure are described in further detail below with reference to examples.

Example 1

The embodiment provides a hybrid membrane camouflaged nanomedicine loaded with oxidative phosphorylation inhibitor and its preparing method thereof.

The preparing method comprises the following steps.

(1) Synthesis of 4-(4,4,5,5-tetramethyl-1,3,2-dioxaborolan-2-yl) benzyl acrylate (HB)

Firstly, 4-(hydroxymethyl) phenylboronic acid pinacol ester was dissolved in dry dichloromethane, transferred to a three-neck flask, and a certain amount of triethylamine was added. Methacryloyl chloride dissolved in anhydrous dichloromethane was added dropwise to a three-necked flask through a constant pressure dropping funnel under ice-bath conditions. After the dropwise addition, the reaction was continued for 10 hours (h) at room temperature with stirring. Insoluble reaction products were removed by filtration, and the filtrate was firstly subjected from rotary evaporator to reduce the volume of dichloromethane, and then diluted with ethyl acetate and washed three times with brine. After drying over magnesium sulfate overnight, the organic solution was purified by silica column chromatography using petroleum ether and ethyl acetate (30:1 by volume) as the eluent.

(2) Synthesis of Methylated Polyethylene Glycol-Dithio Naphthoic Acid-(4-Cyano) Valerate (PEG-CPADN)

CPADN was dissolved in a hydrous tetrahydrofuran, followed by the adding the catalyst N-hydroxysuccinimide (NHS). the N,N'-dicyclohexylcarbodiimide (DCC) in dry tetrahydrofuran was added dropwise to a three-necked flask through a constant pressure funnel at 0° C. After the dropwise addition, the reaction is continued for 24 hours at room temperature, and triethylamine was added to terminate the reaction. Then, methylated polyethylene glycol was added, and the reaction was continued with stirring for 12 hours. After the reaction was finished, the mixture was filtered, rotary evaporated, precipitated and washed three times with cold ethyl ether, and dried in a vacuum overnight to obtain a pink solid product.

(3) Synthesis of the ROS-Responsive Polymer PEG-PHB (i.e., ROS-Responsive Nanocarrier)

Figure 2:
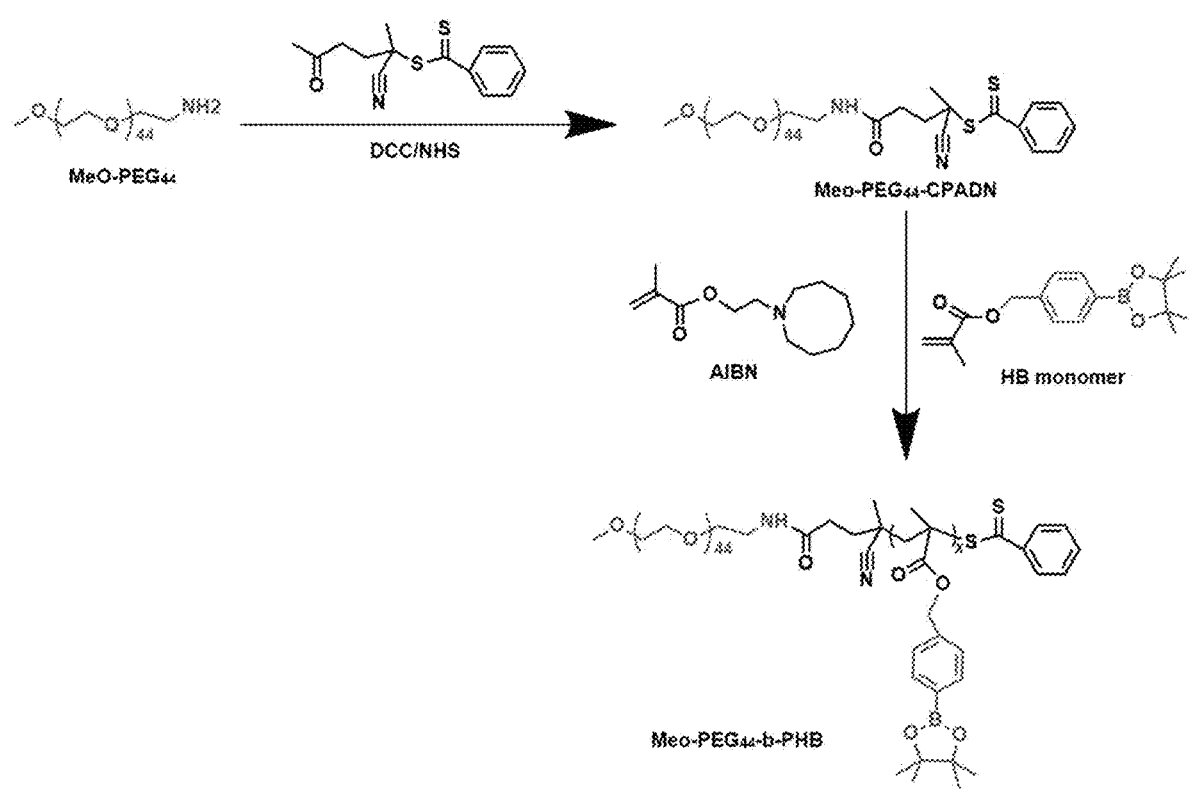
FIG. 2 is the synthesis diagram of PEG-PHB.

The preparation of the PEG-PHB was obtained by reversible addition fragmentation chain transfer polymerization (RAFT) (as shown in FIG. 2). The method comprises the following specific steps: under the protection of nitrogen, HB monomer, PEG-CPADN, Azobisisobutyronitrile (AIBN) as an initiator and 1, 4-dioxane were added into a Schlenk vacuum sealed bottle and reacted for 48 h at 65° C. Excess HB monomer and other unreacted reagents were removed by dialysis.

(4) Preparation of the Mitochondria-Cancer Cell Hybrid Membrane Nanovesicles (HM)

Preparing the cancer cell membrane: the cancer cell membrane was obtained by membrane protein extraction kit. 1 mL of the membrane protein extraction reagent A added with PMSF was added to the collected 2,000-5,000 GBM cells (U87MG). The cells were gently and sufficiently dispersed, and cooled in an ice bath for 10-15 min After that, the cells were subjected to 3 cycles of freezing-thawing. Then, the obtained mixture was centrifuged (700 g, 10 min, 4° C.), and the supernatant was carefully collected into a new centrifuge tube. Subsequently, the supernatant was further centrifuged at 14,000×g for 30 min at 4° C. to precipitate the desired cancer cell membrane fragments (CM).

Mitochondrial membrane was prepared according to the mitochondrial extraction kit. 1-2.5 mL of a mitochondrial isolation reagent added with PMSF was added to 20,000,000-50,000,000 U87MG cells, and the cells were gently dispersed and cooled in an ice bath for 15 min. The cell suspension was transferred to a glass homogenizer of appropriate size and homogenized about 20 times. The cell homogenate was centrifuged at 4° C., 600×g for 10 min. The supernatant was carefully transferred to another centrifuge tube and centrifuged at 4° C., 11,000×g for 10 min. The supernatant was carefully removed. The precipitation was the cell mitochondria. Then, another 150-200 µL of PMSF-added mitochondria lysate was added to lyse mitochondria, and mitochondria membrane (MM) was obtained by ultracentrifugation.

Figure 3:
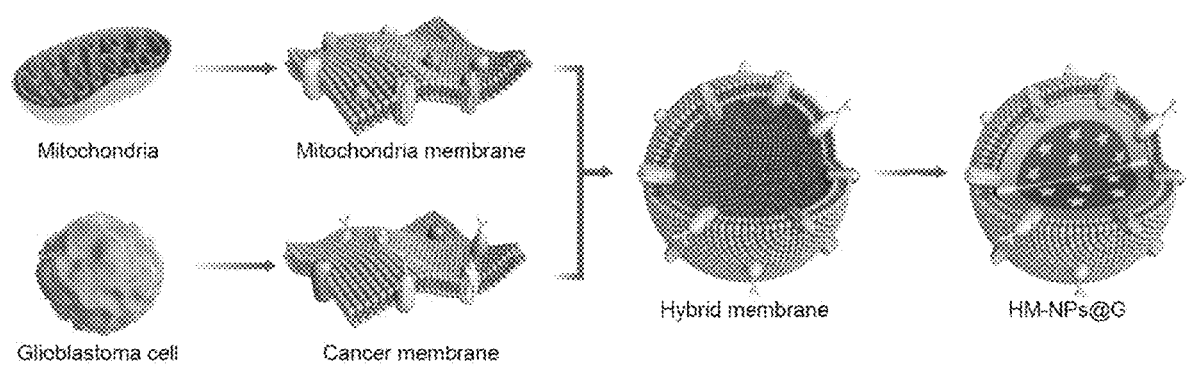
FIG. 3 is the schematic view of the preparation of mitochondria-cancer cell hybrid membrane nanovesicles.

CM and MM was mixed according to a protein weight ratio of 1:1. The sample was sonicated for 2 min in an ice bath, and subsequently extruded through 800 nm, 400 nm, and 200 nm polycarbonate porous membranes using an Avanti mini extruder to facilitate membrane fusion. Finally, the hybrid membrane vesicles (HM) were collected by centrifugation (21,000 g, 30 min, 4° C.) and re-suspended in PBS. (As shown in FIG. 3).

(5) Preparation of the Mitochondria-Cancer Cell Membrane Camouflaged Nanomedicine Loaded with the Oxidative Phosphorylation Inhibitor Preparation of the ROS-responsive nanoparticle and loading of Gboxin: PEG-PHB was dissolved in tetrahydrofuran, Gboxin with corresponding theoretical drug loading capacity was added, free drugs were removed by dialysis, and finally, the ROS-responsive drug-loading nanoparticle (NPs@G) was obtained. The drug loading efficiency (DLE) and drug loading capacity (DLC) of Gboxin were determined by high performance liquid chromatography (HPLC).

Figure 4:
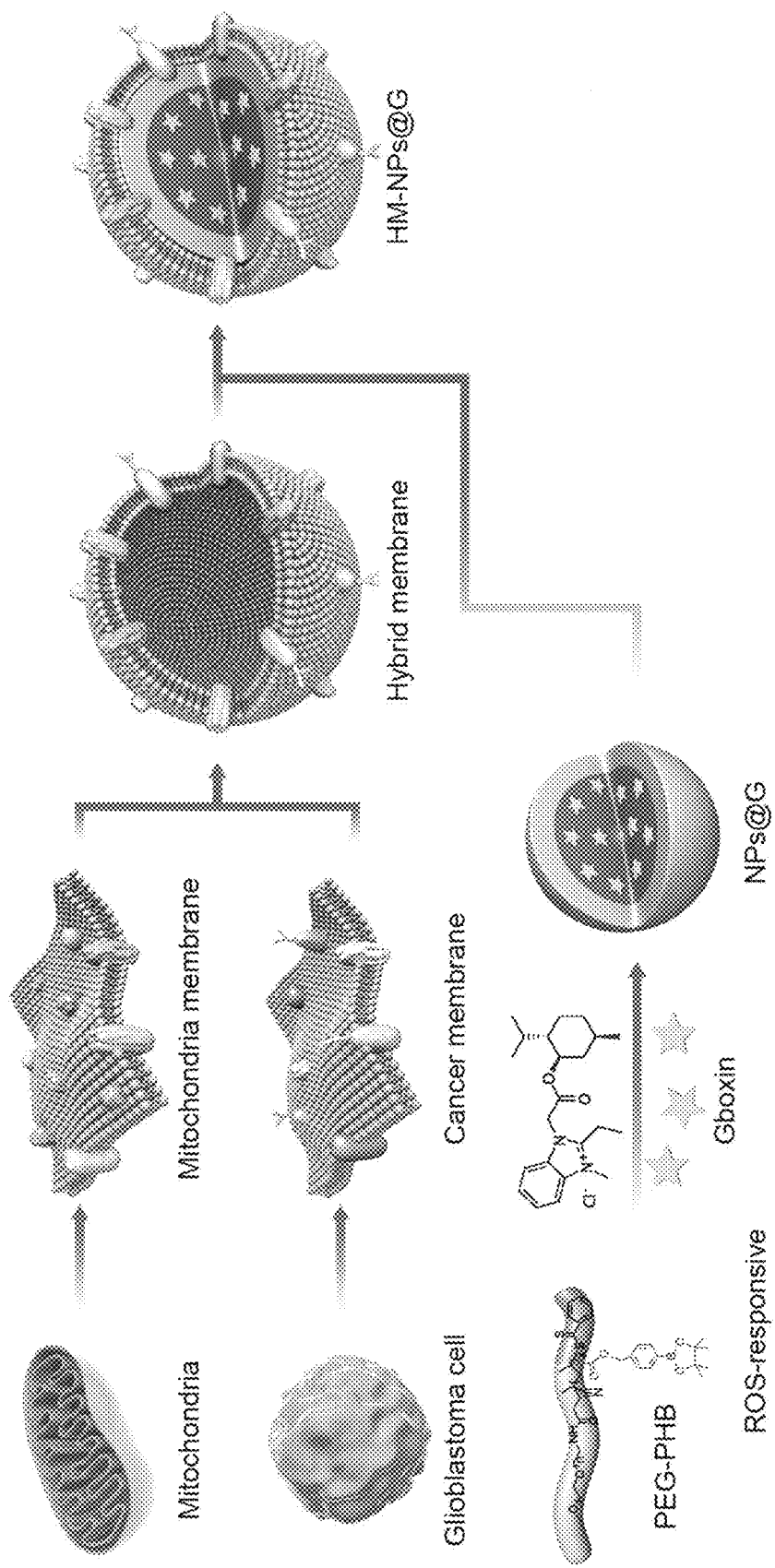
FIG. 4 is the schematic diagram of HM-NPs@G preparation.

NPs@G and HM were mixed according to a certain proportion (1:1), repeatedly extruded 7 times through 400 nm and 200 nm of water-phase filters to obtain HM-NPs@G (as shown in FIG. 4), and the particle size, particle size distribution and structure of the HM-NPs@G was determined by DLS and TEM.

Experimental Example 1

Figure 5:
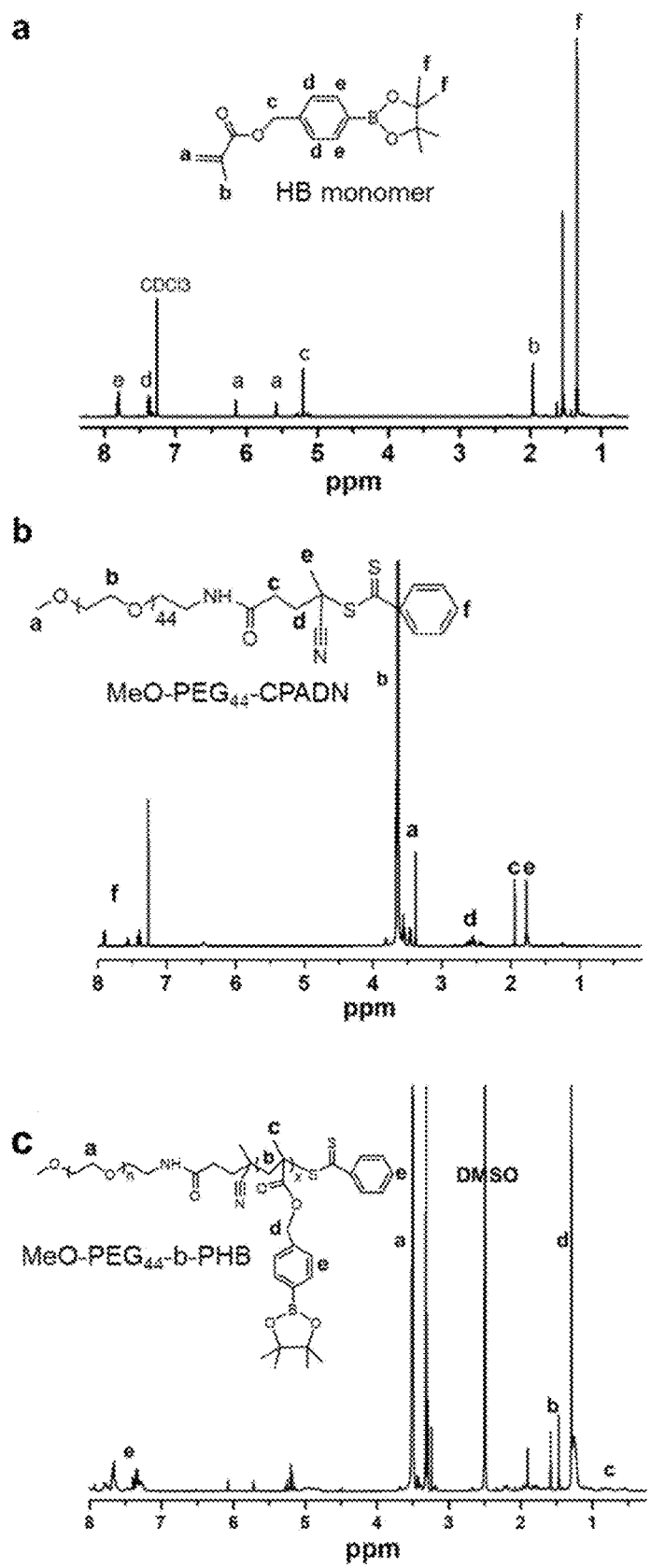
FIG. 5 shows the NMR result of the structural characterization of PEG-PHB.

The experimental example carries out structural characterization on the HB, the PEG-CPADN and the PEG-PHB which are synthesized in the example 1. FIG. 5 is a graph showing the NMR result of structural characterization. (a) 1H-NMR(CDCl$_3$) of the HB, 4-hydroxymethyl phenyl borate and methacryloyl chloride were used as raw materials to synthesize the ROS-sensitive HB monomer with the yield of 80%; (b) 1H-NMR(CDCl$_3$) of PEG-CPADNM, RAFT was activated and reacted with PEG-NH2 at room temperature to generate PEG-CPADN, wherein the grafting rate is 100%; (c) 1H-NMR(DMSO) of synthesized PEG-PHB, PEG-CPADN and HB monomer are reacted through RAFT reaction to obtain the polymer nanocarrier PEG-PHB, the polymerization degree of the PHB is about 11, the polymerization molecular weight is 3.3 k, the total molecular weight of the PEG-PHB is 5.3 k, and the polymerization degree can be obtained through the calculation of the area of the characteristic peak of the nuclear magnetic result.

Experimental Example 2

Figure 6:
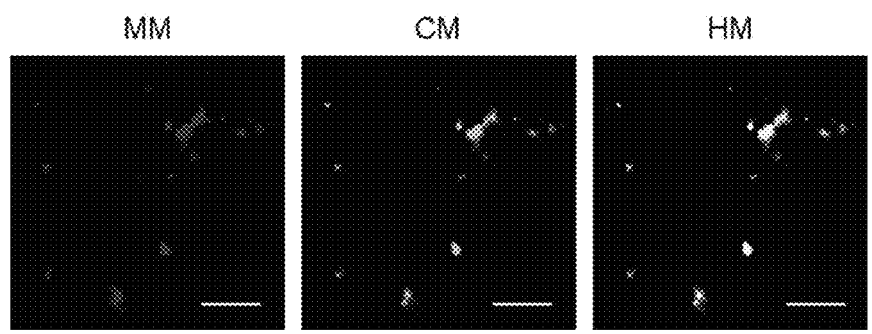
FIG. 6 is a image of confocal laser scanning microscope (CLSM) of the mitochondria-cancer cell hybrid membrane.

In this experimental example, the fluorescence resonance energy Transfer (FRET) technique was used to verify the hybrid membrane nanovesicles, and as shown in FIG. 6, the scale bar was 10 µm, the mitochondria membrane (MM) was stained with DiI (red fluorescence), the cancer cell membrane (CM) was stained with DiR (green fluorescence), and the overlapping showed yellow by confocal observation, which proved that the mitochondrial-cancer cell hybrid membrane nanovesicles were successfully prepared.

Experimental Example 3

In this experimental example, the mitochondria-cancer cell membrane camouflaged and the oxidative phosphorylation inhibitor loaded nanomedicine prepared in example 1 was subjected to HPLC to detect the drug loading efficiency (DLE) and the drug loading capacity (DLC) of Gboxin, and was subjected to DLS and TEM to detect the particle size distribution and structure of the nanoparticles.

Figure 7:
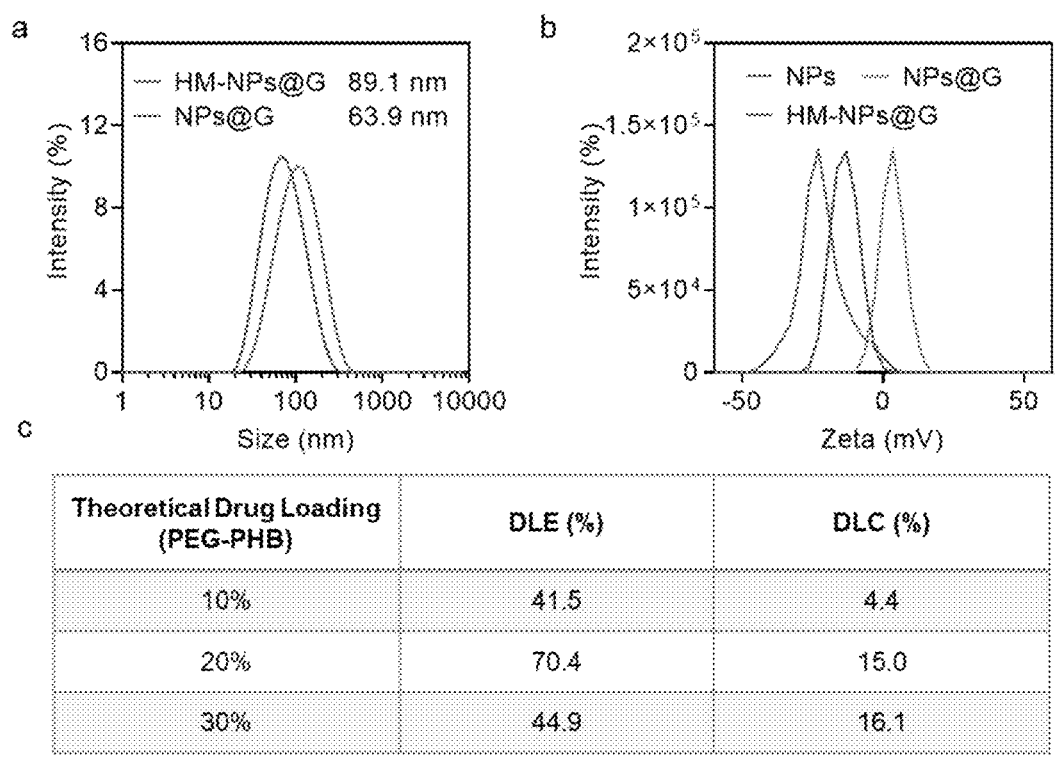
FIG. 7 shows the size distribution and structure as well as the drug loading capacity of the nanomedicine.

The experimental results are shown in FIG. 7, in which (a) is particle sizes of NPs@G and HM-NPs@G; (b) is Zeta surface potentials for NPs, NPs@G and HM-NPs@G; (c) is the DLC and the DLE of the nanoparticles. PEG-PHB can self-assemble in water solution to form stable nanoparticles with particle size of 63.9 nm; and after being coated by the hybrid membrane, the particle size was 89.1 nm (FIG. 7a), potential was changed to −30 mV (FIG. 7b) from +5 mV, and DLS test shows that the nanoparticle size distribution is uniform. Encapsulation efficiencies were 41.5%, 70.4%, and 44.9% at theoretical drug loading capacities of Gboxin of 10%, 20%, and 30%, respectively, as determined by HPLC (FIG. 7c).

Experimental Example 4

This example was used to perform an in vitro drug release experiment. The experimental procedure was as follows: incubating nanomedicines in the environments imitating tumor cells and mitochondria with a high level of ROS ($H2O2$, 100 μM, 1 mM), and monitoring changes of particle size and particle size distribution of the nanoparticles by DLS. In vitro release experiments were performed at 37° C., 600 μL of HM-NPs@G was dialyzed in 25 mL of PBS buffer solution with or without $H_2O_2$. At the set time point, 5 mL of release medium was withdrawn and replaced with the same volume of fresh medium. The amount of Gboxin in the release medium was determined by HPLC. The release result was the average of three replicates.

Figure 8:
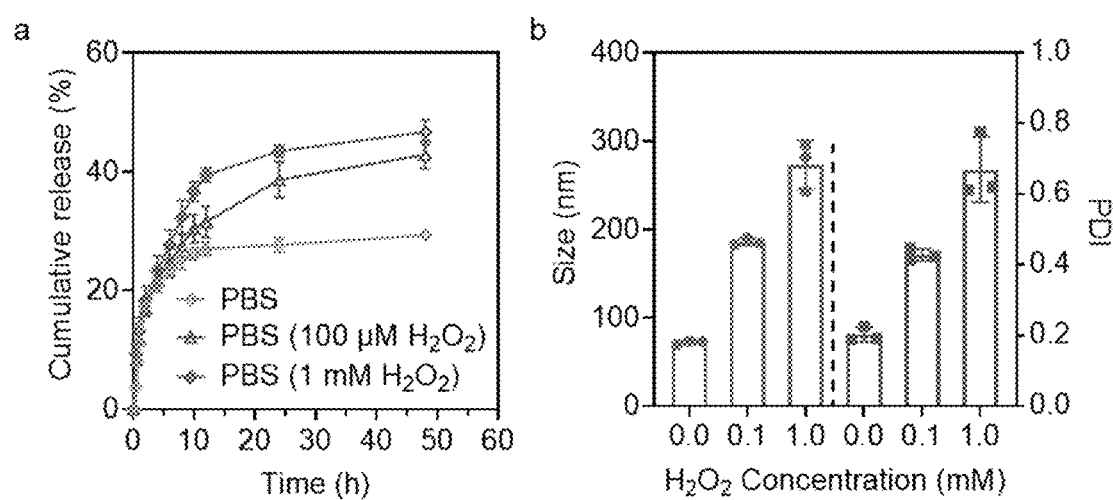
FIG. 8 shows the result of in vitro ROS-responsive release.

The results of in vitro release experiments are shown in FIG. 8. FIG. 8a is the Gboxin release results of HM-NPs@G at various concentrations of $H_2O_2$. In the PBS without $H_2O_2$ at 37° C., the Gboxin release amount was low; and in the PBS with 100 μM and 1 mM $H_2O_2$, the 48 h Gboxin release amount was obviously increased, which was due to the release of the drug caused by the swelling of nanoparticles under the oxidizing condition. In addition, FIG. 8b shows the changes of particle size and PDI of HM-NPs@G at various concentrations of $H_2O_2$, and as compared with the group of nanoparticles without $H_2O_2$, the particle size and PDI of HM-NPs@G incubated in the $H_2O_2$ medium were significantly increased. This means that HM-NPs@G simultaneously solves the two big problems of leakage and slow release in cells of the traditional biodegradable nanomedicine.

Experimental Example 5

In this experimental example, cellular uptake and intracellular release were characterized by flow cytometry and CLSM.

In flow cytometry assay, U87MG cells were seeded in 6-well plates (1×10$^6$ cells/well) and incubated for 24 h at 37° C. Then HM-NPs@Cy5, MM-NPs@Cy5, CM-NPs@Cy5, NPs@Cy5, or free Cy5 were added (Cy5 concentration 10 μg/mL) and incubated for 6 h, and the sample was removed and the cells were digested with tyrisin. The cell suspension was centrifuged at 1,000×g for 3 min, washed twice with PBS, re-dispersed in 500 μL PBS, and recorded using flow cytometry (BD FACS Calibur, Becton Dickinson, USA) within 1 h, and then the result was analyzed by Cell Quest software based on 10,000 gated events.

Figure 9:
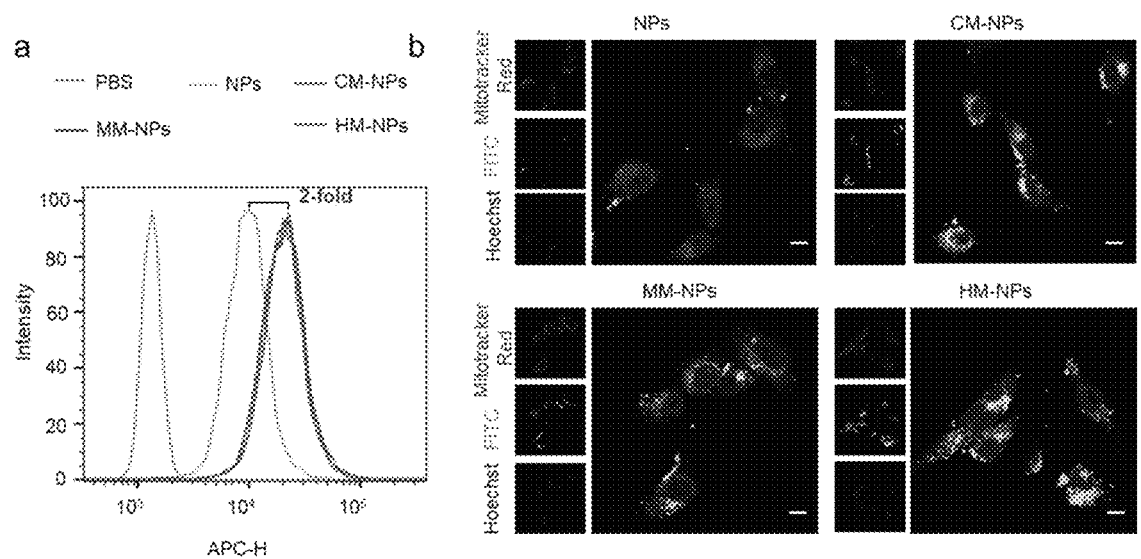
FIG. 9 shows the results of flow cytometry and CLSM.

The flow cytometry experiment (FIG. 9a) result proves that the HM-NPs has a higher endocytosis efficiency which is 2 times of that of non-enveloped NPs control groups.

The cellular uptake and intracellular drug release behavior were also observed by CLSM. The U87MG cells were cultured on microscope slides in 12-well plates (1×10$^5$ cells/well) for 24 h. Then 50 μL of HM-NPs@FITC, MM-NPs@FITC, CM-NPs@FITC, or NPs@FITC in PBS were added (FITC concentration: 10 μg/mL). After 6 h incubation, the medium was removed, and the cells were washed twice with PBS. Nucleis were stained with Hoechst33342 (10 μg/mL) for 10 min and washed twice. Fluorescence images were taken by CLSM (Zeiss LSM 880).

CLSM (FIG. 9b) observes that after being incubated with the HM-NPs for 6 h, U87-MG cells have stronger FITC fluorescence, which proves that HM-NPs have stronger GBM cell specificity homologous targeting capability and are effectively transported into tumor cells.

Experimental Example 6

This example was used for cytotoxicity test.

Figure 10:
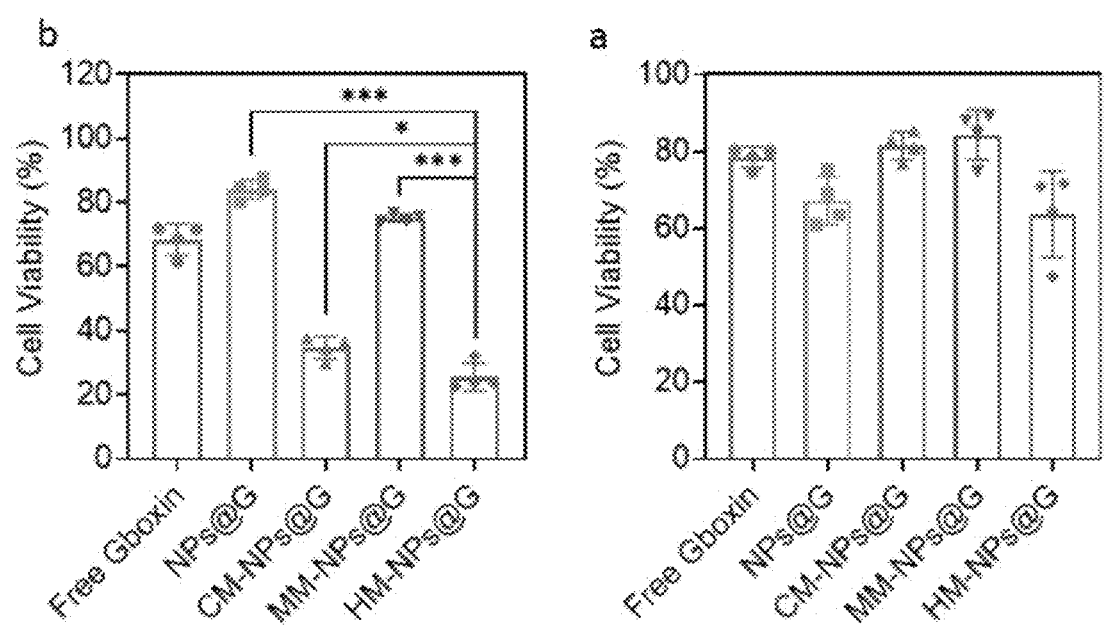
FIG. 10 shows the result of cytotoxicity assay.

U87MG or CSC-2 cells were plated in 96-well plates (1×10$^3$ cells/well) for 24 h, then the culture medium was removed and replenished with 90 μL of fresh culture medium and 10 μL of empty nanoparticles, and incubated for 96 h. Then, 10 μL of CCK-8 solution (5 mg/mL) was added. After incubation for another 40 min, the absorption of each well at a wavelength 450 nm was measured by a microplate reader (Devices/13×, Molecular Device, USA). Cells treated with PBS were used as controls. Four sets (n-4) were made in parallel for each experimental data. FIG. 10a is the biocompatibility of the unloaded nanoparticles with U87MG and CSC-2.

U87MG or CSC-2 cells were plated in 96-well plates (1×103 cells/well) for 24 h, and then the culture medium was removed and replenished with 90 μL of fresh culture medium and 10 μL of nano-drugs HM-NPs@G, MM-NPs@G, CM-NPs@G, NPs@G loaded with Gboxin and free Gboxin, and the final concentration of Gboxin was 800 nM. After incubation for 96 h, 10 μL of CCK-8 solution (5 mg/mL) was added, and the sample was incubated for 40 min. Then the absorption of each well at a wavelength of 450 nm was measured by a microplate reader. Cells treated with PBS were used as controls. Four sets (n-4) were made in parallel for each experimental data.

The result shows that the HM-NPs is still nontoxic to U87MG and CSC2 cells even when the concentration of polymers is up to 0.8 mg/mL (FIG. 10a), which proves the good biocompatibility of the HM-NPs. As expected, HM-NPs@G shows the most significant antitumor activity against U87-MG and CSC-2 cells when compared to the other control groups (FIG. 10b shows the killing effect of different nanomedicines on U87MG and CSC-2 cells (Gboxin concentration: 800 nM)).

Experimental Example 7

ATP activity detection was performed.

U87MG or CSC-2 cells were seeded in 24-well plates (1×10$^5$ cells/well) and incubated overnight. Subsequently, 50 μL of HM-NPs@G, MM-NPs@G, CM-NPs @G, NPs@G and free Gboxin were added, and the final concentration of Gboxin was 800 nM. After further incubation for 96 h, the cells were washed twice with 1×PBS and lysed with ATP lysate, centrifuged for 5 min at 4° C. and 12,000×g after lysis, and the supernatant was taken. Then, the supernatant was combined with ATP detection working solution, and ATP in cell lysate was determined by using a microplate reader and the ATP standards.

Figure 11:
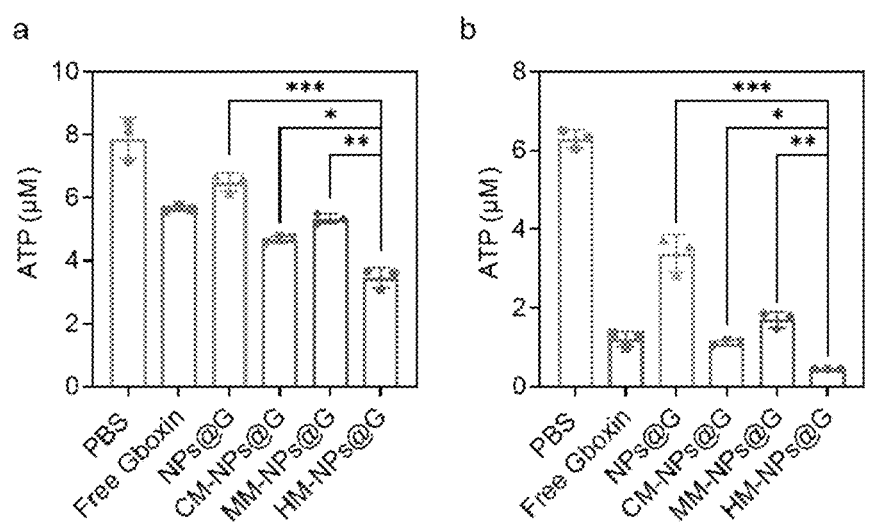
FIG. 11 shows the results of intracellular ATP activity and level detection.

It should be noted that Gboxin is an ATP synthase inhibitor to inhibit ATP synthase activity, so that ATP synthesis is inactivate, resulting in a decrease in ATP synthesis. The result in FIG. 11 shows that in U87MG and CSC-2 cells, the amount of ATP in the HM-NPs@G group was most significantly reduced when compared to the other control groups. This result also provides evidence that the biomimetic nanomedicines can indeed kill tumor cells by reducing ATP synthesis.

Experimental Example 8

Mitochondrial membrane potential detection was performed.

Mitochondrial membrane potential changes in tumor cells were measured using fluorescent probe JC-1. The U87MG cells were seeded on a glass slide at the bottom of a 12-well plate at a density of 1×105 cells per well, and were incubated overnight. Subsequently, 50 µL of HM-NPs@G, MM-NPs@G, CM-NPs@G, NPs@G and free Gboxin were added, and the final concentration of Gboxin was 800 nM. After being further incubated for 96 h, 200 µL JC-1 staining buffer was added, and the sample was incubated at 37° C. for 20 min. Then, the staining buffer was removed, and the cells were washed for three times with pre-cooled JC-1 washing buffer (1×). 4% of paraformaldehyde was added for fixation for 15 min, and the cells were washed twice with 1×PBS, followed by addition of Hoechst33342 (10 µg/mL) as a nuclear staining solution, was incubated for 10 min, and was washed twice with 1×PBS. The cell slides were taken out from the 12-well plate by a pair of tweezers reversely buckled on a glass slide coated with the anti-fade mounting medium, and detected by CLSM.

Figure 12:
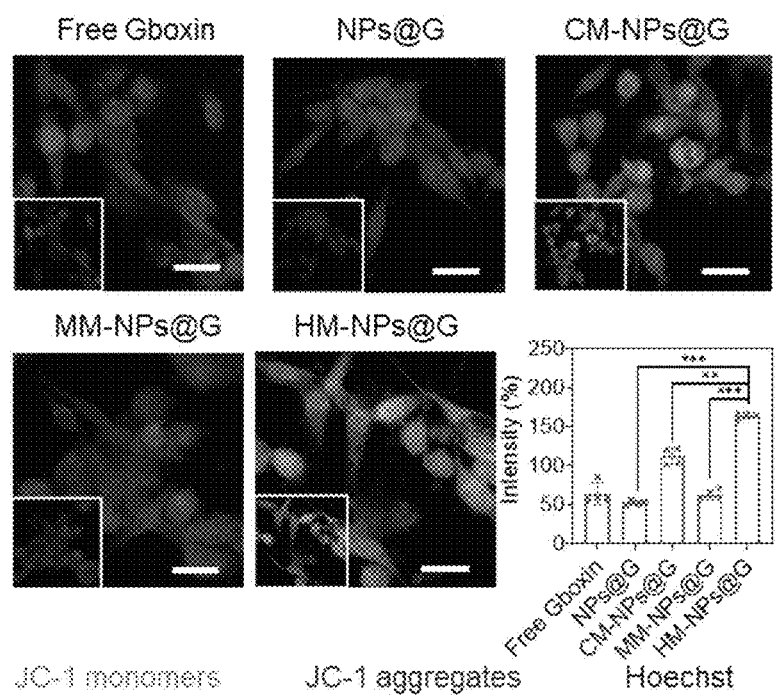
FIG. 12 shows mitochondrial membrane potential in U87MG cells treated with different nanomedicines including HM-NPs@G.

Inactivation of ATP synthase not only results in a decrease in ATP synthesis, but also results in a decrease in mitochondrial membrane potential. The changes of mitochondrial membrane potential were measured by JC-1 mitochondrial membrane potential probe, in which JC-1 exists in the form of aggregates and exhibits red fluorescence in normal cells, while JC-1 becomes a monomeric form and exhibits green fluorescence when the mitochondria membrane potential is reduced. The CLSM results (FIG. 12) clearly show that the green fluorescence of U87MG cells treated by HM-NPs@G is strongest, indicating that the mitochondrial membrane potential is significantly reduced.

Experimental Example 9

Proteins Level was Detected by Western Blotting (WB)

U87MG cells were seeded in 6-well plates at 2×10⁵ cells per well and incubated for 24 h. Then, 200 µL of HM-NPs@G, MM-NPs@G, CM-NPs@G, NPs@G and free Gboxin were added, respectively, and the final concentration of Gboxin were 800 nM. Cells treated with PBS were used as controls. After the sample being incubated for 96 h, the nanoparticles were removed, and the cells were washed 3 times with 1×PBS buffer, followed by trypsinization and collection of the cells. The collected cells were lysed with RIPA (strong) cell lysate (Beyotime, China) containing 1 mM PMSF, and then the protein loading volume was determined by detecting the protein concentration of each group with BCA protein concentration detection kit (Beyotime, China). Lysates were separated by electrophoresis (SDS polyacrylamide gel) and transferred to PDVF membranes (Beyotime, China). PDVF membranes were treated with antibody against caspase-3/9, cleaved caspase-3/9, and cytochrome C (cell signaling technology, 9662s, 9502s, 9664s) (Abcam, ab133504), and were incubated overnight at 4° C. Then, the PVDF membranes were incubated with IRDye800CW secondary antibody for 1 h. Subsequently, the immunoreactive bands were visualized by enhanced chemiluminescence (Licor, USA). The experiment takes β-Actin as a housekeeping protein control.

Figure 13:
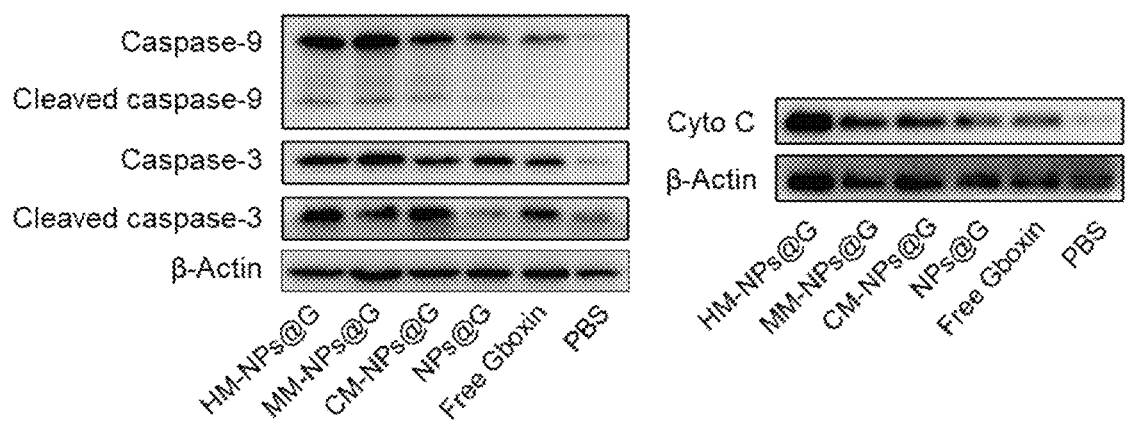
FIG. 13 shows the expression levels of cytochrome C and apoptosis-related proteins in U87MG cells treated with different nanomedicines such as HM-NPs@G.

The reduction of the mitochondrial membrane potential can promote cytochrome C to enter cytoplasm, and the transfer of the cytochrome C to the cytoplasm can stimulate cascade caspase reaction and activate apoptotic protein families (caspase 3 and caspase 9). Cytochrome C and apoptotic protein families are important indicators of tumor cell apoptosis. The western blotting results in FIG. 13 show that the expression level of cytochrome C was highest in the HM-NPs@G group cells, and the expression levels of Caspase 3, Caspase 9, cleavedcaspase-9 and cleaved-caspase-3 were significantly increased correspondingly. The results further demonstrate that apoptosis is regulated by the mitochondrial intrinsic apoptosis pathway. In summary, HM-NPs@G can deliver more Gboxin to mitochondrial target sites, thereby significantly reducing mitochondrial membrane potential and finally activating apoptosis of tumor cells.

Experimental Example 10

Pharmacokinetics experiment was performed.

In the in vivo pharmacokinetic study, BALB/c mice of 6-8 weeks were randomized into groups (3 in parallel per group). Each mouse was administrated with 200 µL of HM-NPs@G, MM-NPs@G, CM-NPs@G, or free Gboxin (Gboxin dose of 5 mg/kg) by tail vein injection, and blood was taken from the retro-orbital sinus at predetermined time points. The blood samples were weighted and extracted with organic solvents, and the drugs were quantified by HPLC. The pharmacokinetic parameters of the drug in vivo such as the elimination half-life (t½, β), the area under the drug concentration-time curve (AUC), the clearance rate (CL) can be calculated by software fitting, and the pharmacokinetic parameters are compared with the nanomedicines without the coating of mitochondria-cancer cell membrane one by one, so that the blood stability of the biomimetic nanomedicines can be investigated.

Figure 14:
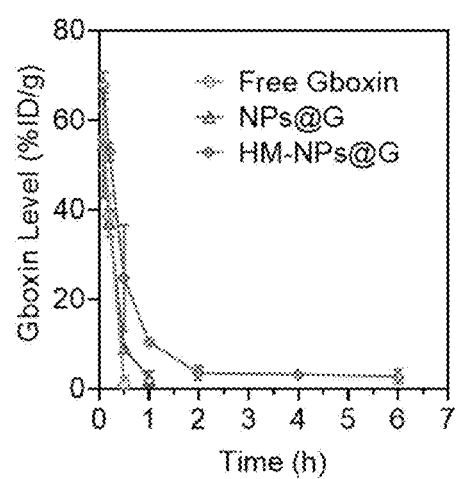
FIG. 14 shows the result of in vivo pharmacokinetics.

The result of in vivo pharmacokinetics (FIG. 14) shows that the circulation time in vivo of HM-NPs@G is prolonged, which is longer than NPs@G and free Gboxin, indicating that the cell membrane modifying helps nanoparticles escape from the nonspecific recognition and blood clearance, extending the circulation time.

Experimental Example 11

Anti-tumor effect in vivo was detected.

U87MG orthotopic GBM model was established by implantation of tumor tissue into the brain of BALB/c nude mice (18-20 g, 6-8 weeks). The average biological fluorescence intensity used for the therapeutic experiment was 1×10⁵-5×10⁵, and the average biological fluorescence intensity used for biodistribution experiment was 1×10⁶-5×10⁶.

The in-situ model was established by using luciferase-labeled human brain glioma cells (U87MG-Luc), the multi-dose administration was performed by a tail vein injection, and the tumor luminescence intensity was monitored by the Lumina IVIS III system. The relative photon flux was normalized to initial intensity, I/I0 (I0 is the bioluminescence intensity at day 7). The body weight of mice was individually measured every three days and the Kaplan-Meier survival curve was recorded during the period. After the treatment was finished, the health condition of major organs and the apoptosis condition of tumor tissues of mice after treatments of different nanomedicines and free Gboxin were analyzed by histological staining such as H&E and TUNEL. Through the treatment, it can be concluded that the mitochondria-cancer cell hybrid membrane camouflaged nanomedicines have negligible systemic toxicity and robust anti-tumor activity on U87 MG-Luc GBM-bearing nude mice.

Figure 15:
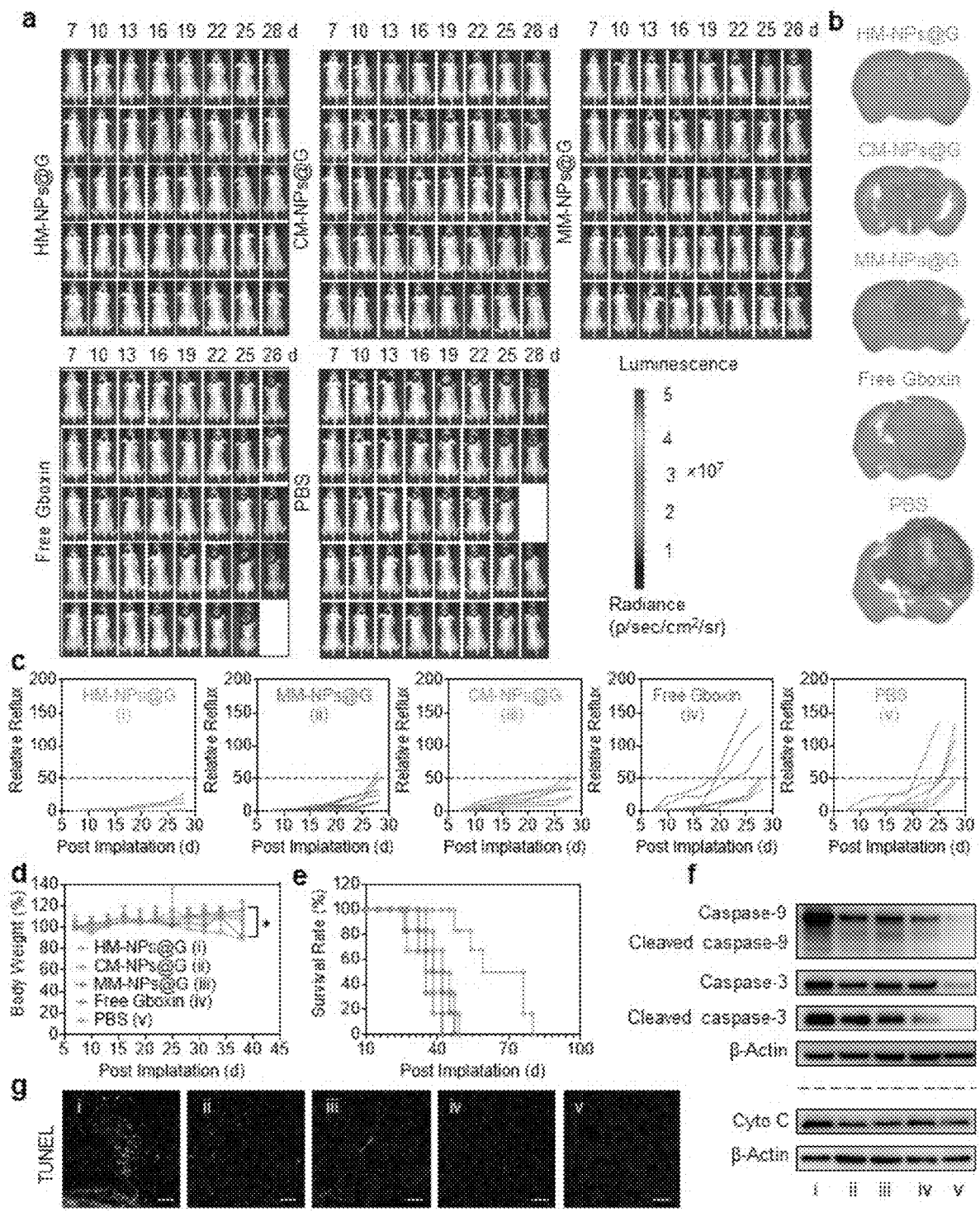
FIG. 15 shows the in vivo therapeutic effects of different nanomedicines such as HM-NPs@G on tumor-bearing mice.

Results of the treatment shows that the U87MG-Luc orthotopic GBM bearing mice treated with HM-NPs@G for five times of tail vein administration (3 mg/kg) have the optimal anti-glioma effect. Specifically, the tumor growth is significantly inhibited (FIG. 15a, b). The bioluminescence quantification result also demonstrates that HM-NPs@G significantly better inhibited tumor growth than the other controls (FIG. 15c). In addition, the Kaplan-Meier survival curve (FIG. 15e) shows that HM-NPs@G greatly extends the survival time of the mice, with a median survival of 63 days, significantly longer than MM-NPs@G, CM-NPs@G, free Gboxin and PBS. In vivo western blot result (FIG. 15f) also demonstrates that HM-NPs@G can effectively induce tumor cell apoptosis by promoting cytochrome C release and activating apoptotic protein families. The TUNEL result (FIG. 15g) also demonstrates that HM-NPs@G can efficiently kill GBM cells through apoptosis.

Figure 16:
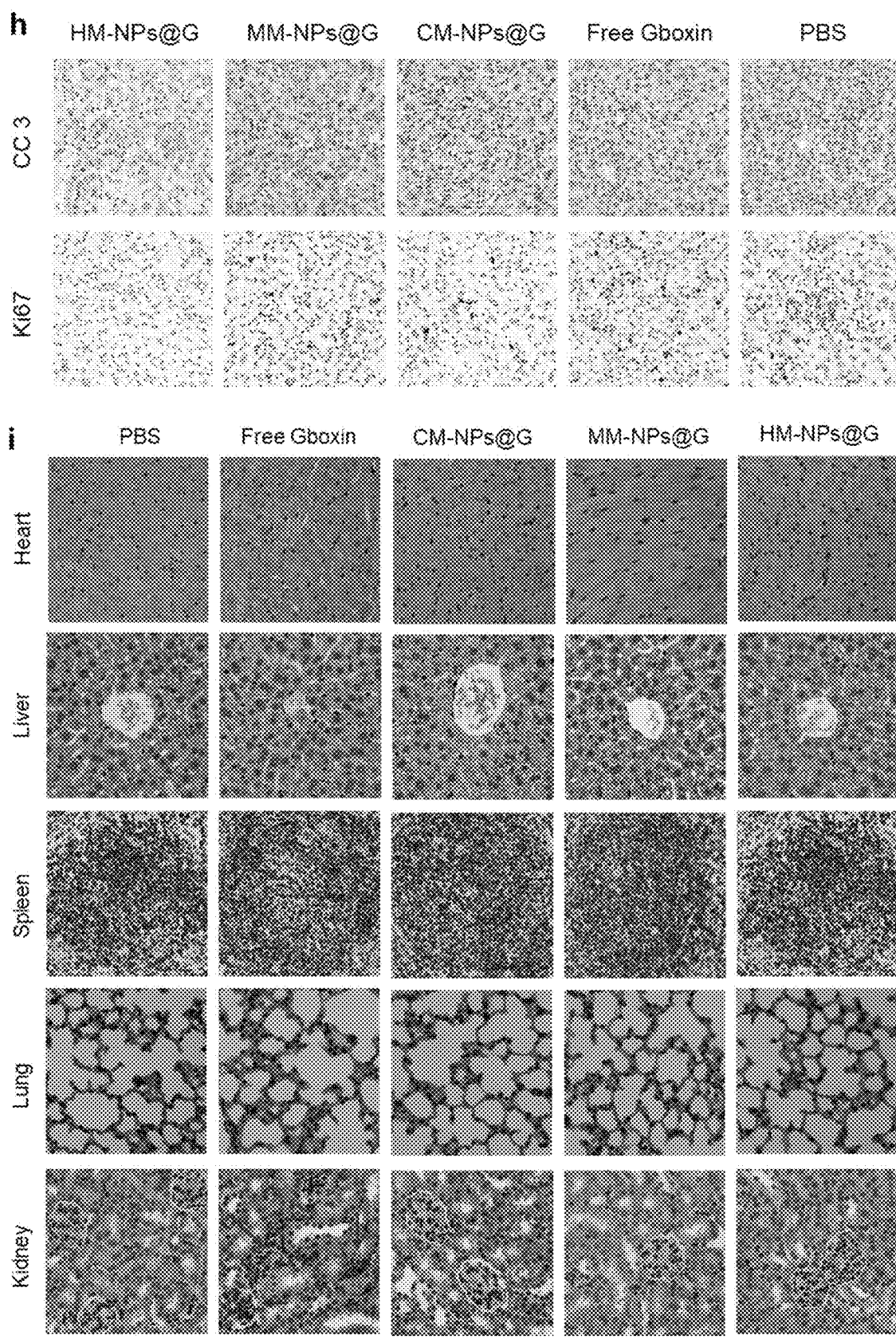
FIG. 16 shows the H&E staining of various organs of mice after administering different nanomedicines such as HM-NPs@G.

FIG. 16h shows that the apoptotic protein expression levels of the cleaved caspase 3 (cc3) is increased, indicating that HM-NPs@G can effectively promote the apoptosis of tumor cells; and the expression level of Ki67, one of proliferation factors, is reduced as shown in FIG. 16h, proving that HM-NPs@G can effectively inhibit proliferation.

Histological analysis of H&E staining demonstrates that HM-NPs@G had minimal damage to major organs including heart, liver, spleen, lung, and kidney when administered at 3 mg Gboxin/kg (FIG. 16i). The result indicates that HM-NPs@G has very good biocompatibility.

Experimental Example 12

BBB penetration and tumor targeting were detected.

In the in vivo imaging, Gboxin was replaced by near-infrared dye DiR. Different nanoparticles and free DiR were injected into U87MG-Luc human GBM orthotopic mice. At predetermined time points post intravenous i.v. injection, the distribution of nanoparticles and free DiR was monitored by a near-infrared fluorescence imaging system IVIS Lumia III. The accumulation and retention at brain tumor positions were repeatedly investigated, and by qualitative and quantitative comparison between the naked NPs group and the single-membrane coated groups, BBB crossing efficiency and tumor targeting capacity were investigated.

Figure 17:
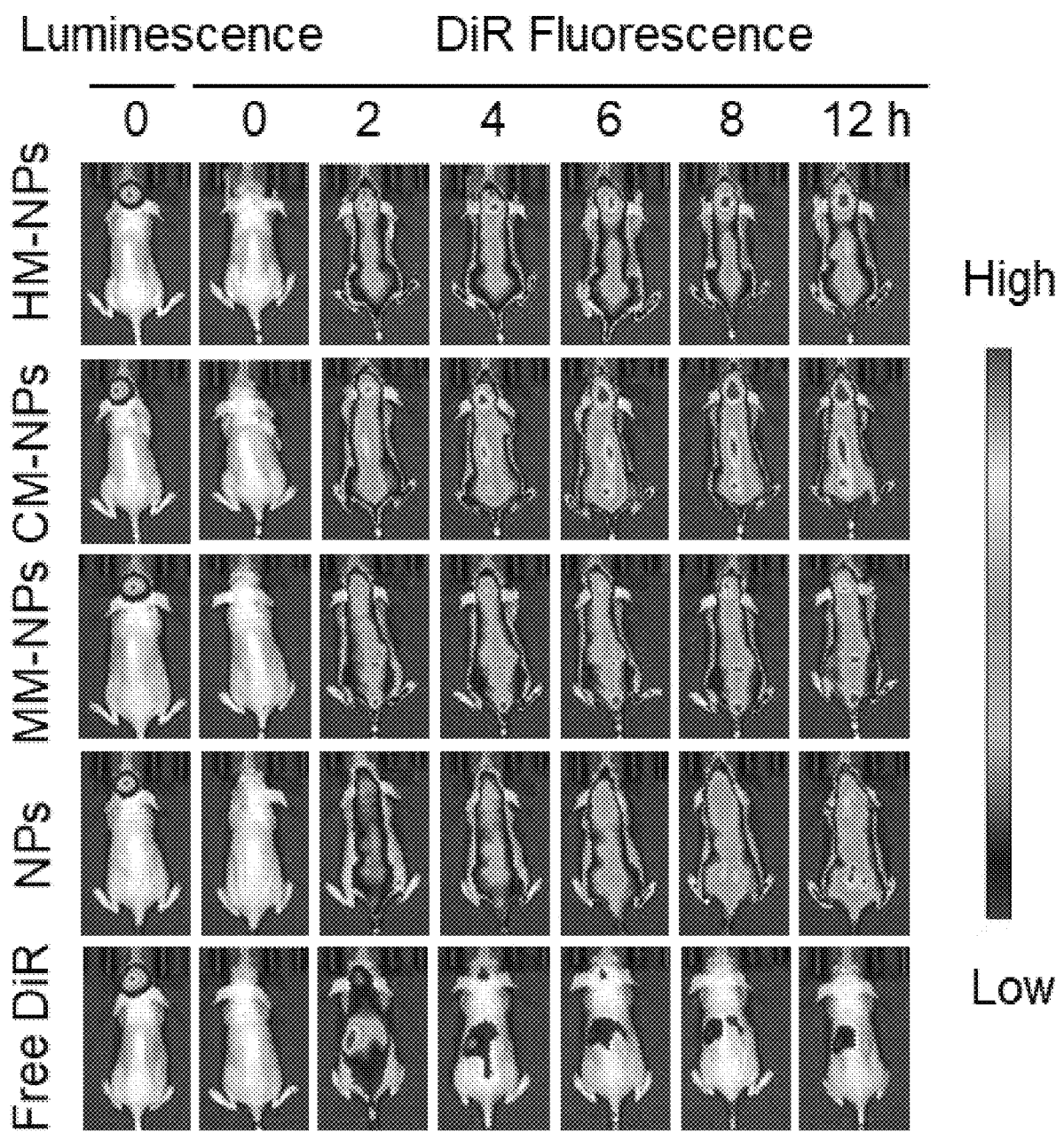
FIG. 17 shows the fluorescence intensity of mice treated with HM-NPs@DiR and other nanoparticles at different time points.

The result (FIG. 17) of the distribution of nanoparticles at different time points in vivo monitored by the IVIS Lumia III system shows that the fluorescence intensity in GBM tumor sites of HM-NPs is significantly higher than that of the control groups, indicating that the HM-NPs has good ability of homologously targeting tumors.

The above description is only a preferred embodiment of the disclosure and is not intended to limit the disclosure, and various modifications and changes may be made by those skilled in the art. Any modification, equivalent replacement, or improvement made within the spirit and principle of the disclosure shall be included in the protection scope of the disclosure.

What is claimed is:

1. A mitochondria-cancer cell hybrid membrane camouflaged nanomedicine loaded with oxidative phosphorylation inhibitor, comprising an inner core and an outer shell, wherein the outer shell is coated on a periphery of the inner core, wherein the inner core comprises a ROS-responsive drug-loading nanoparticle and a drug loaded by the ROS-responsive drug-loading nanoparticle, wherein the drug is the oxidative phosphorylation inhibitor, and wherein the outer shell is a hybrid membrane of a mitochondria membrane and a cancer cell membrane;

wherein the ROS-responsive drug-loading nanoparticle comprises polyethylene glycol-poly(β-butyrolactone) having a following structural formula:

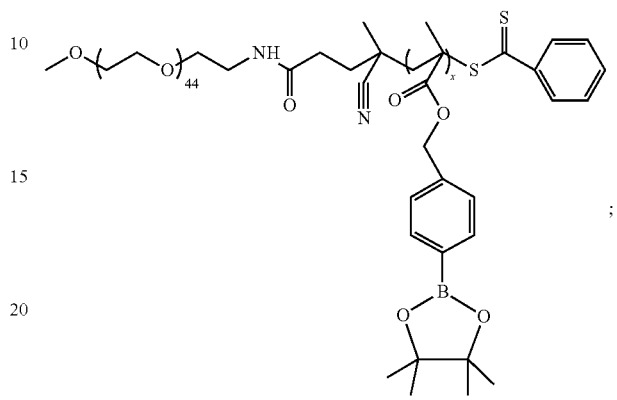

wherein a polymerization degree x of poly(β-butyrolactone) in the polyethylene glycol-poly(β-butyrolactone) is 8-12.

2. The mitochondria-cancer cell hybrid membrane camouflaged nanomedicine loaded with oxidative phosphorylation inhibitor of claim 1, wherein the oxidative phosphorylation inhibitor is Gboxin.

3. The mitochondria-cancer cell hybrid membrane camouflaged nanomedicine loaded with oxidative phosphorylation inhibitor of claim 1, wherein a molecular weight of the poly(β-butyrolactone) is $2.4 \times 10^3$-$3.6 \times 10^3$, and a total molecular weight of the polyethylene glycol-poly(β-butyrolactone) is $4.4 \times 10^3$-$5.6 \times 10^3$.

4. The mitochondria-cancer cell hybrid membrane camouflaged nanomedicine loaded with oxidative phosphorylation inhibitor of claim 1, wherein a drug loading capacity of the oxidative phosphorylation inhibitor in the inner core is 4.4%-36%.

5. The mitochondria-cancer cell hybrid membrane camouflaged nanomedicine loaded with oxidative phosphorylation inhibitor of claim 2, wherein a drug loading capacity of Gboxin in the inner core is 4.4%-36%.

6. The mitochondria-cancer cell hybrid membrane camouflaged nanomedicine loaded with oxidative phosphorylation inhibitor of claim 1, wherein the cancer cell membrane is derived from a GBM cell or a glioma stem cell.

7. The mitochondria-cancer cell hybrid membrane camouflaged nanomedicine loaded with oxidative phosphorylation inhibitor of claim 1, wherein a protein weight ratio of the mitochondrial membrane to the cancer cell membrane is 1:1.

8. The mitochondria-cancer cell hybrid membrane camouflaged nanomedicine loaded with oxidative phosphorylation inhibitor of claim 1, wherein a mass ratio of the inner core to the outer shell is 1:1; and an average particle size of the inner core is 50-70 nm, and an average particle size of the mitochondria-cancer cell hybrid membrane camouflaged nanomedicine loaded with oxidative phosphorylation inhibitor is 80-100 nm.

9. A preparing method for the mitochondria-cancer cell hybrid membrane camouflaged nanomedicine loaded with oxidative phosphorylation inhibitor of claim 1, comprising:

mixing the mitochondria-cancer cell hybrid membrane with the inner core so that the mitochondrial-cancer cell hybrid membrane is coated on the outer periphery of the inner core.

10. The preparing method for the mitochondria-cancer cell hybrid membrane camouflaged nanomedicine loaded with oxidative phosphorylation inhibitor of claim 9, further comprising: preparing the outer shell, wherein preparing the outer shell comprises mixing, ultrasonic treatment and/or extrusion of the mitochondria membrane and the cancer cell membrane.

11. The preparing method for the mitochondria-cancer cell hybrid membrane camouflaged nanomedicine loaded with oxidative phosphorylation inhibitor of claim 9, further comprising: preparing the inner core, wherein preparing the inner core comprises mixing of the oxidative phosphorylation inhibitor and a ROS-responsive high-molecular polymeric nanocarrier, stirring and/or dialysis.

12. The preparing method for the mitochondria-cancer cell hybrid membrane camouflaged nanomedicine loaded with oxidative phosphorylation inhibitor of claim 11, wherein the ROS-responsive high-molecular polymeric nanocarrier is dissolved in a water miscible solvent, being added with the oxidative phosphorylation inhibitor, followed by stirring until a reaction is completed and dialysis to remove a free oxidative phosphorylation inhibitor.

13. The preparing method for the mitochondria-cancer cell hybrid membrane camouflaged nanomedicine loaded with oxidative phosphorylation inhibitor of claim 10, wherein the ultrasonic treatment is carried out for 8-10 min at an ultrasonic frequency of 100-110 W and a temperature of 36-38° C.

14. The preparing method for mitochondria-cancer cell hybrid membrane camouflaged nanomedicine loaded with oxidative phosphorylation inhibitor of claim 10, wherein the extrusion is performed through a series of water-phase filters.

15. The preparing method for the mitochondria-cancer cell hybrid membrane camouflaged nanomedicine loaded with oxidative phosphorylation inhibitor of claim 14, wherein the extrusion is repeatedly performed for 7 times through the water-phase filters with pore sizes of 800 nm, 400 nm and 200 nm in turn.

16. A method for preparing a drug for treatment of a tumor or a mitochondrial apoptosis activator, comprising:

generating the mitochondria-cancer cell hybrid membrane camouflaged nanomedicine loaded with oxidative phosphorylation inhibitor of claim 1.

17. The method of claim 16, wherein the tumor is GBM.

18. The method of claim 16, wherein the oxidative phosphorylation inhibitor for activating mitochondria apoptosis is an inhibitor that promotes changes in mitochondrial membrane potential and/or an inhibitor that inhibits ATP synthase activity.

19. An inner core for a mitochondria-cancer cell hybrid membrane camouflaged nanomedicine loaded with oxidative phosphorylation inhibitor, wherein the inner core comprises a ROS-responsive drug-loading nanoparticle and a drug loaded by the ROS-responsive nanoparticle, wherein the drug is the oxidative phosphorylation inhibitor;

wherein the ROS-responsive drug-loading nanoparticle comprises polyethylene glycol-poly($\beta$-butyrolactone) having a following structural formula:

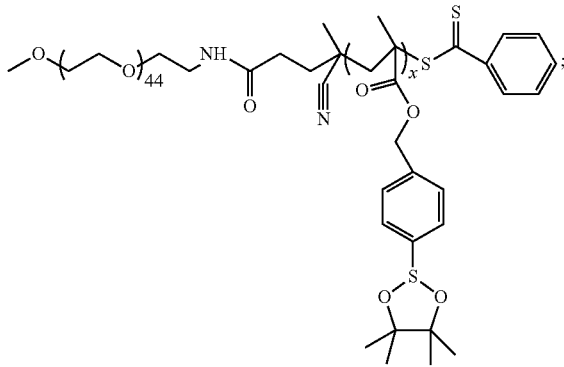

wherein a polymerization degree x of poly($\beta$-butyrolactone) in the polyethylene glycol-poly($\beta$-butyrolactone) is 8-12.

20. The inner core for the mitochondria-cancer cell hybrid membrane camouflaged nanomedicine loaded with oxidative phosphorylation inhibitor of claim 19, wherein the oxidative phosphorylation inhibitor is Gboxin.

* * * * *